United States Patent [19]

Carlson et al.

[11] Patent Number: 5,693,004

[45] Date of Patent: Dec. 2, 1997

[54] CONTROLLABLE FLUID REHABILITATION DEVICE INCLUDING A RESERVOIR OF FLUID

[75] Inventors: J. David Carlson, Cary, N.C.; Mark D. Grabiner, Shaker Heights, Ohio

[73] Assignees: Lord Corporation, Cary, N.C.; The Cleveland Clinic Foundation, Cleveland, Ohio

[21] Appl. No.: 610,796

[22] Filed: Mar. 11, 1996

[51] Int. Cl.$^6$ ..................................................... A61H 1/00
[52] U.S. Cl. .............................. 601/23; 601/40; 601/166; 600/9; 600/13
[58] Field of Search .................... 600/9, 13, 14, 600/10, 15; 601/15, 17, 23, 40, 55, 148, 151, 160, 166; 607/104, 108–114, 86; 482/44, 49, 55, 111

[56] References Cited

U.S. PATENT DOCUMENTS

| | | | |
|---|---|---|---|
| 2,580,232 | 12/1951 | Landauer | 607/86 |
| 3,286,711 | 11/1966 | MacLeod . | |
| 3,565,065 | 2/1971 | Biggs, Jr. . | |
| 3,786,526 | 1/1974 | Ausseil . | |
| 3,867,929 | 2/1975 | Joyner et al. . | |
| 4,063,561 | 12/1977 | McKenna | 600/12 |
| 4,583,530 | 4/1986 | Henley . | |
| 4,759,544 | 7/1988 | Diat | 482/111 |
| 4,767,118 | 8/1988 | Ostergard . | |
| 4,819,951 | 4/1989 | Solloway . | |
| 4,830,360 | 5/1989 | Carr, Jr. . | |
| 4,907,574 | 3/1990 | Hollerbach . | |
| 5,277,281 | 1/1994 | Carlson et al. . | |
| 5,284,330 | 2/1994 | Carlson et al. . | |
| 5,368,544 | 11/1994 | Tran et al. | 600/9 |
| 5,382,373 | 1/1995 | Carlson et al. . | |
| 5,398,917 | 3/1995 | Carlson et al. . | |
| 5,409,435 | 4/1995 | Daniels | 482/73 |
| 5,425,690 | 6/1995 | Chang . | |
| 5,441,477 | 8/1995 | Hargest | 601/15 |
| 5,460,585 | 10/1995 | Gentry et al. . | |
| 5,509,888 | 4/1996 | Miller | 600/29 |
| 5,518,495 | 5/1996 | Kolt | 600/13 |

FOREIGN PATENT DOCUMENTS

| | | | |
|---|---|---|---|
| 453602 | 10/1991 | European Pat. Off. | 600/13 |
| 1692577 | 11/1991 | U.S.S.R. | 601/55 |

OTHER PUBLICATIONS

Carlson et al.; MR Fluid Devices and Process of Controlling Force in Exercise Equipment Utilizing Same; S/N—08/304,005.
Weiss et al.; High Strength Magneto–and Electro–rheological Fluids; SAE 932451.
Carlson et al.; Commercial Magneto–rheological Fluid Devices; Jul. 1995.
Lord Corporation; Rheonetic™ Systems: A New Dimension in Vibration Control; Brochure Aug. 1994.
Lord Corporation; VersaFlo™ Controllable Fluids; Brochure PL01–2000A.
Hammacher Schlemmer Catalog Advertisement; Late Winter 1996.

*Primary Examiner*—Jeanne M. Clark
*Attorney, Agent, or Firm*—Richard K. Thomson; Randall S. Wayland; James W. Wright

[57] ABSTRACT

A controllable fluid device (20) for rehabilitation of injured or weakened complex appendages such as the hands and feet. The controllable fluid device (20) includes a reservoir (34) which contains a sufficient amount of controllable fluid (52) such as a Magnetorheological (MR) fluid. A magnetic field generator (36) provides the magnetic field (H) which is applied to the controllable fluid (52) by a magnetic circuit (60). In one aspect, an electromagnet including a coil (58) and core (54) provides the magnetic field (H). The intensity of the magnetic field is controlled via a controller (38). In another aspect, the magnetic field (H) is provided by a permanent magnet (44) and a mechanical shunt mechanism (42) is used to vary the magnetic field intensity. Other embodiments include a heater unit (66) with optional thermostat (74).

15 Claims, 7 Drawing Sheets

CONTROLLABLE FLUID REHABILITATION DEVICE INCLUDING A RESERVOIR OF FLUID

FIELD OF THE INVENTION

The present invention relates to devices which are useful in rehabilitation of injured or weakened human body parts. More specifically, the present invention relates to controllable devices for rehabilitation use.

BACKGROUND OF THE INVENTION

Joint mobility dysfunction, contractures or muscle weakness may develop as a result of injury, surgeries, vascular or neurological problems, illness or the like. For rehabilitation of such joint mobility dysfunction and muscle weakness, physical therapy is required. The therapist generally uses manipulation and heat therapy to improve mobility of the affected joint and/or muscles. Notably, for injuries to complex multiple-degree-of-freedom portions of the body, such as the hands and feet, there are few mechanical devices which can aid in their rehabilitation. The reason for this is because there are so many different degrees of freedom of movement. In the hands, for instance, there is flexion, extension, abduction and adduction motions. Mechanical devices would become exceedingly complex if they were to attempt to exercise all of these different mobilities.

Therapists have used hot wax vats, which the patient would immerse their hands into, and exercise their hands therein. Although, they could exercise multiple degrees of mobility, wax would have to be removed from their hands after immersion. Further, there is no controllability of the level of resistance applied and only a small resistance force is derived from the melted wax. Therefore, there is a recognized need for a device for providing therapeutic exercise to complex dysfunctional and/or weakened appendages. In particular, there is a long felt and unmet need for a rehabilitation device for such complex appendages as hands and feet. In particular, there is a need for a device which can rehabilitate and strengthen the extensor muscles of the hand.

SUMMARY OF THE INVENTION

In light of the advantages and drawbacks of the prior art, the present invention is a controllable fluid rehabilitation device including a reservoir of controllable fluid for rehabilitation of immersed human body parts (examples include hands and feet) comprising a housing having a reservoir formed therein for containing a sufficient volume of a magnetically controllable fluid for immersion of the injured or weakened body part. The magnetically controllable fluid is of the type which experiences a change in apparent viscosity when exposed to a magnetic field. This change in viscosity provides the resistive forces experienced by the user as they immerse their appendage into the reservoir of magnetically controlled fluid and flex the appendage therein. The magnetic field is developed by a magnetic field generator and acts on the controllable fluid in such a way as to change its apparent viscosity. A magnetic circuit directs the magnetic field such that it acts through the controllable fluid to bring about the change in apparent viscosity. Preferably, the level of resistance experienced by the user may be variably adjusted. Both permanent magnet and electromagnet generators are described herein. In another aspect, a therapeutic heating element is incorporated which may also include a thermostat.

It is an advantage of the present invention that it provides controllability of the level of resistance felt by the user.

It is another advantage of the present invention that it provides therapeutic exercise of the extensor muscles in the hand.

The above-mentioned and further details and advantages of the present invention will become apparent from the accompanying descriptions of the preferred embodiments and attached drawings.

BRIEF DESCRIPTION OF THE DRAWING

The accompanying drawings which form a part of the specification, illustrate several key embodiments of the present invention. The drawings and description together, serve to fully explain the invention. In the drawings.

DETAILED DESCRIPTION OF THE INVENTION

Figure 1:
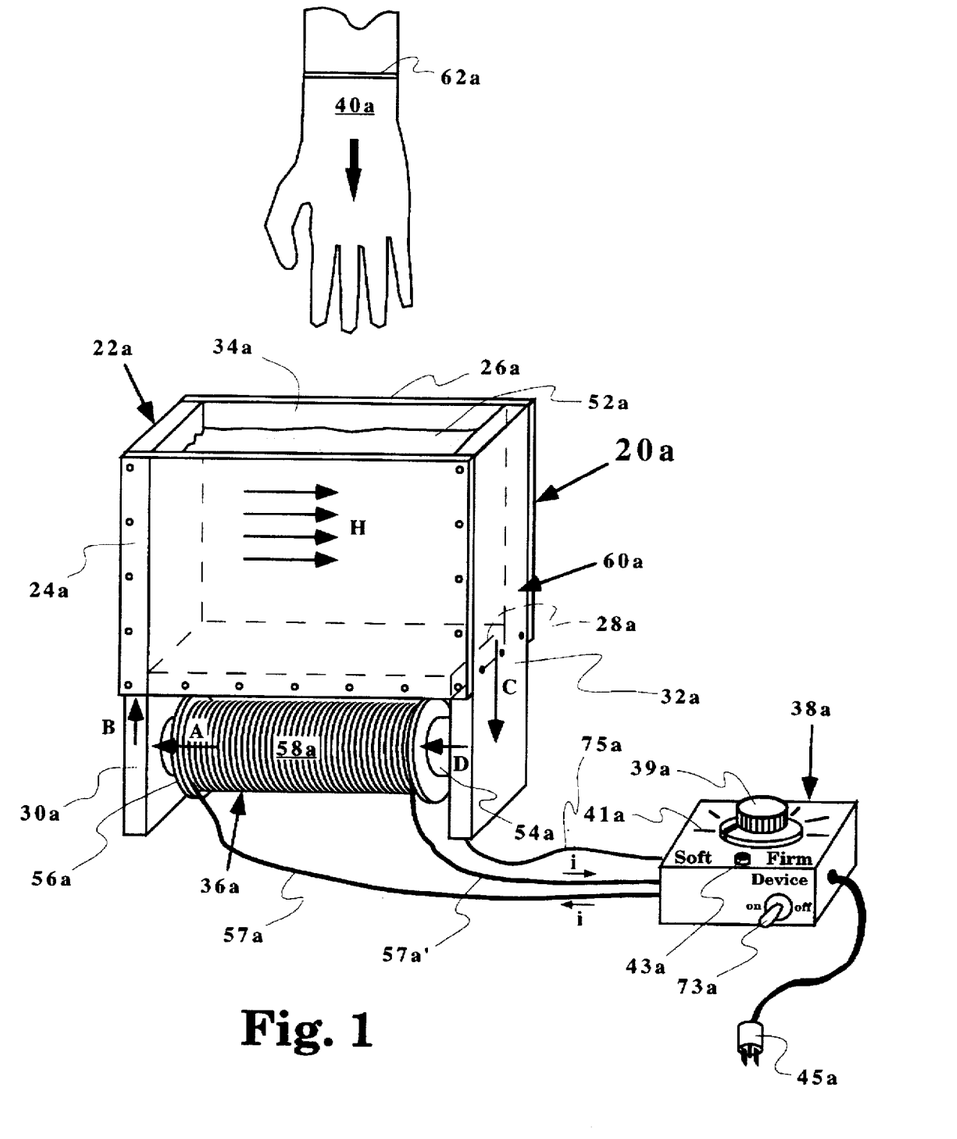
FIG. 1 is an isometric view of a first embodiment of the controllable fluid rehabilitation device including a reservoir of magnetically controllable fluid into which the user immerses the appendage to be rehabilitated and wherein the magnetic field generator includes an electromagnet.

Referring now to the Drawings where like numerals denote like elements. As best shown in FIG. 1, shown generally at 20a is a first embodiment of a controllable fluid rehabilitation device which includes a magnetically controllable fluid such as a Magnetorheological (MR) fluid. MR fluids include a carrier fluid such as silicone oil, mineral oil, synthetic hydrocarbon oil, or water with fine magnetic particles dispersed therein. MR fluids are described in commonly assigned U.S. Pat. No. 5,382,373 invented by Carlson and Weiss entitled "Magnetorheological Materials Based on Alloy Particles" and U.S. patent application Ser. No. 08/544,689 invented by Carlson and Jones-Guion entitled "Aqueous Magnetorheological Materials." The disclosures of each are hereby incorporated by reference herein.

The device 20a is comprised of a housing 22a, which is preferably box-like and includes a front 24a, a back 26a which are manufactured from a non-magnetic material such as aluminum or plastic and are plate-shaped, a first side 30a and second side 32a which are manufactured from magnetic materials such as low carbon steel or the like which exhibits high magnetic permeability and are also preferably plate-like, and a bottom 28a which is manufactured from a non-magnetic material such as aluminum or plastic. Although shown flat, the bottom may be curved to reduce the weight of fluid required. The housing 22a has formed therein a reservoir 34a for containing a sufficient amount of controllable fluid 52a such as an MR fluid. For example, if a patient's hand 40a were to be rehabilitated, then there would need to be enough controllable fluid 52a to immerse the injured portion of hand 40a therein. Preferably, the user would wear a glove 62a, which may be a disposable rubber glove or the like.

The device 20a also includes a magnetic field generator 36a for generating the magnetic field H. Magnetic circuit 60a provides the means for directing the magnetic field H in a direction such that it acts across or through the volume of controllable fluid 52a contained in the reservoir 34a. In particular, MR fluids experience a change in apparent viscosity when exposed to a magnetic field H. In conjunction with the present invention, it is particularly desirable to use a controllable fluid 52a, such as an MR fluid for the controllable medium. Notably, persons of ordinary skill in the art would be able to envision using other magnetically controllable fluids for accomplishing similar results.

The magnetic circuit 60a is comprised of the first side 30a, the second side 32a, the rod-like core 54a and the fluid 52a. The magnetic field generator 36a is comprised of a core 54a, a bobbin 56a and coil 58a. The core 54a is preferably manufactured from highly permeable material such as low carbon steel and is preferably solid and rod-shaped. A non-metallic bobbin 56a, which is preferably plastic, has a large number of coils of coated copper magnet wire 57a, 57a' or the like wound thereon for forming the coil 58a. By way of example, and not by limitation, the coil 58a preferably would be manufactured from approximately 1000 turns of 18 gauge magnet wire and have a coil resistance of about 15 ohm. Preferably, the area of the core 54a would be about 5.0 sq. in. Further, the area of the first side 30a and second side 32a would be approximately equal to the cross-sectional area of the core 54a and also be about 5.0 square in. Keeping the cross-sectional area approximately equal is thought to prevent saturation of the magnetic field. Directing current i through the coil 58a produces a magnetic field H (according to the famous right hand rule).

The magnetic Field H roughly behaves approximately according to the relationship: H=in/gap, where i=current in amps flowing through the coil 58a, n=the number of coils of wire in the coil 58a, and gap=the distance across the fluid 52a between the first and second sides 30a and 32a. Notably the gap should be minimized as much as possible, yet still allowing users' a gap distance suitable for allowing a full range of flexion. The magnetic flux lines are directed through the core 54a as shown by arrow A, then into the first end 30a as shown by arrow B, then through the fluid 52a, causing an apparent change in viscosity (making the fluid thicker and more viscous) as shown by arrows H, then into end 32a as shown by arrow C and finally back into core 54a as shown by arrow D. These elements complete the magnetic 15 circuit 60a.

The controller 38a may be adjusted by the user by rotating dial 39a (which adjusts a voltage divider to variably control the current directed to the coil) to the appropriate setting 41a which ranges between a Soft and a Firm setting. On Soft, the user will experience only slight resistance to movement of the appendage (such as hand 40a). On the Firm setting, the user will experience significant resistance. An indicator light 43a indicates when the device 20a is properly powered. Grounded plug 45a plugs into standard 110V AC to provide power. An AC to DC converter contained in the controller 38a provides that between about DC 12 volts and about DC 30 Volts and direct current are applied to the coil 58a. The device 20a may be left On by appropriate switching of switch 73a and set to a Soft setting such that a low level of magnetic field is constantly exposed to the fluid 52a such that settling of the particles in the fluid 52a is reduced or eliminated. The device 20a preferably includes a ground wire 75a attached to one of the sides 30a or 32a or bottom 28a.

Figure 2A:
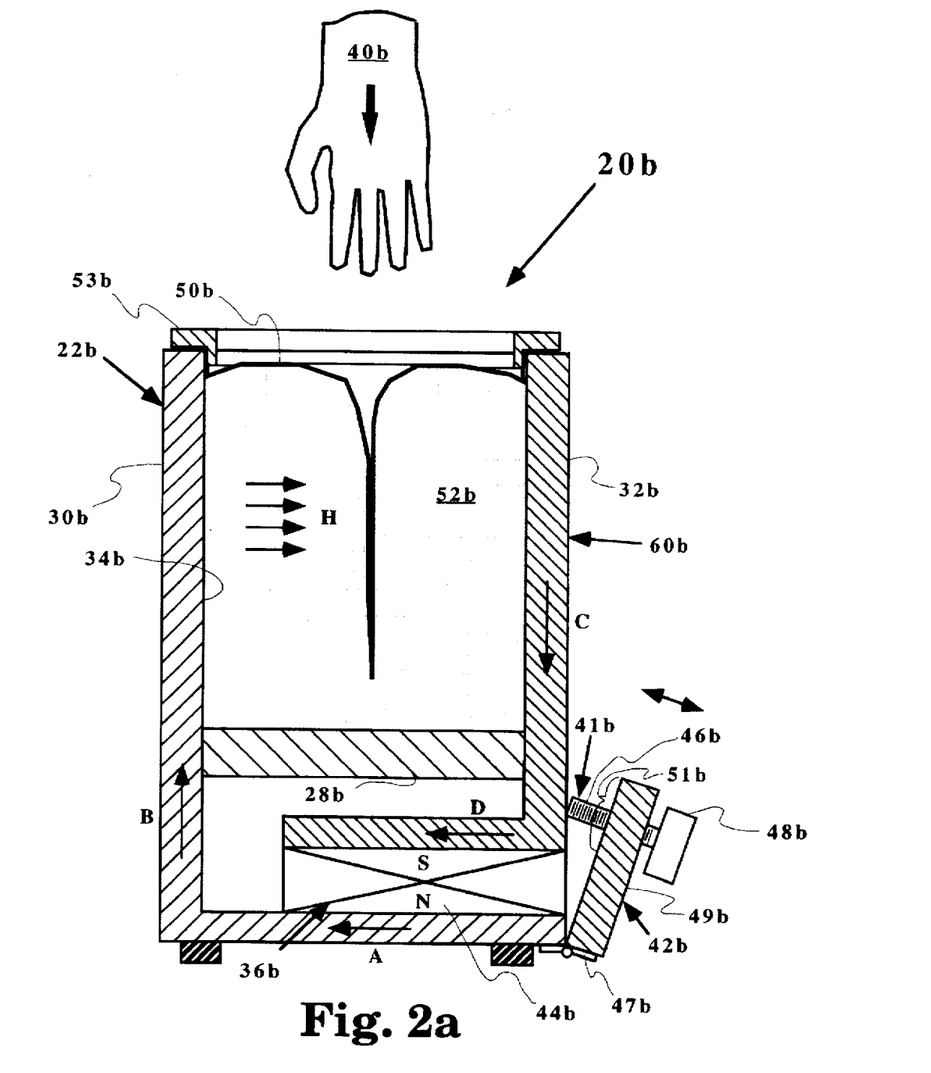
FIG. 2a is a cross-sectional side view of another embodiment of rehabilitation device including a permanent magnet which further includes a mechanical shunt mechanism for controlling the amount of resistance experienced by the user and a flexible partition.

Shown at FIG. 2a, generally at 20b, is another embodiment of controllable fluid rehabilitation device which includes a controllable fluid 52b such as an MR fluid. The device 20b is comprised of a housing 22b which is preferably box-like and which includes a reservoir 34b for containing a sufficient amount of controllable fluid 52b. The major difference being that the magnetic field generator 36b, in the embodiment, is a simple permanent magnet 44b having a north pole N and south pole S. The magnetic circuit 60b is comprised of a first side 30b, a second side 32b, the permanent magnet 44b and the controllable fluid 52b. The back and front (not shown), and bottom 28b are manufactured from non-magnetic materials and are not part of the magnetic circuit 60b. A flexible partition 50b or bladder-like member is used to separate the user's hand 40b from direct contact with the controllable fluid 52b. Retainer 53b is press fit into housing to properly position and secure the partition 50b to the housing 22b.

Preferably, a shunt 42b provides the means for controlling the level of magnetic field H intensity which is directed through the controllable fluid 52b. The shunt 42b is comprised of a plate 49b, manufactured from a high magnetic permeability material such as low carbon steel, which is pivotally attached to the first side 30b by way of hinge 47b and an adjuster 41b which includes a threaded rod 46b with knob 48b secured thereto. Threaded rod 46b is received in a threaded hole formed in plate 49b. A right hand thread is cut on threaded rod 46b such that clockwise (CW) rotation of knob 48b moves the top end 51b of plate 49b further away from second side 32b. By adjusting the shunt 42b, a magnetic short is engaged or disengaged for reducing or increasing the level of magnetic field H intensity which is contained in the magnetic circuit 60b, thereby adjusting the apparent viscosity change of the fluid 52b which is experienced by the user.

Figure 2B:
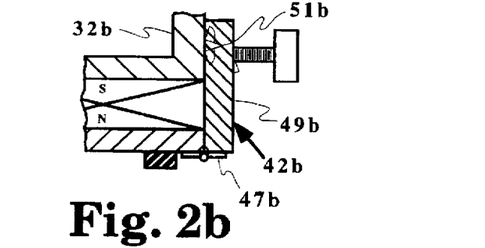
FIG. 2b is a reduced cross-sectional side view of the shunt mechanism shown in the closed position.

When the top end 512b of plate 49b is in close proximity to the second side 32b, as shown in FIG. 2b, the magnetic field H is the least intense and the user encounters little resistance to movement, i.e., because the magnetic circuit 60b is shunted. Contrarily, when the top end 51b is at its furthest point away from the right side 32b, the magnetic field H intensity is the highest and the user experiences a significant resistance to mobility when the appendage, such as hand 40b, is inserted into the reservoir 34b of fluid 52b. The shunt 42b may be set at a setting such that a low level of magnetic field is continuously exposed to the fluid 52b such that settling of the particles in the fluid 52b is reduced or eliminated during periods of non-use.

Figure 3:
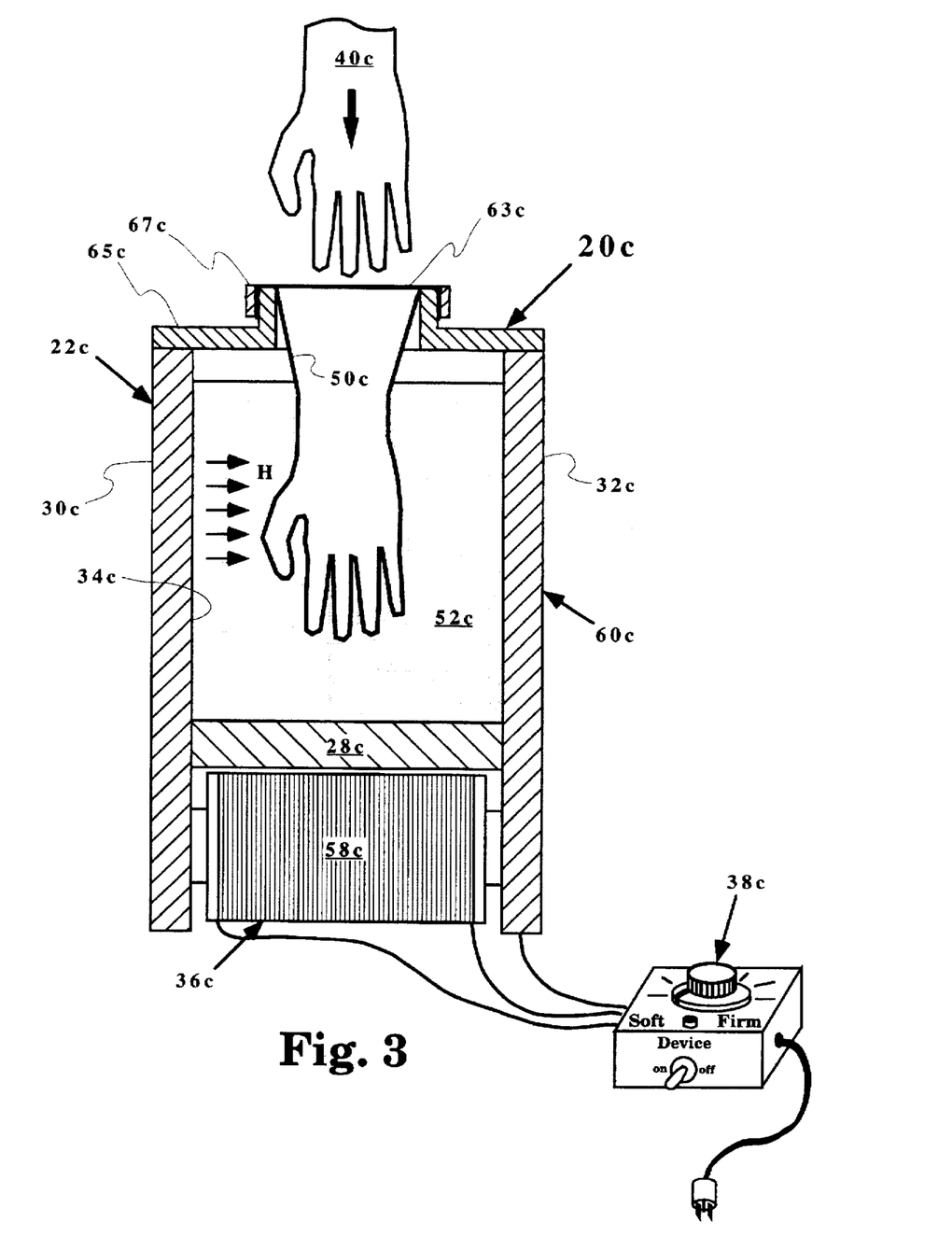
FIG. 3 is a cross-sectional side view of another embodiment of the rehabilitation device wherein the flexible partition is a flexible glove attached to the housing such that the user's skin does not come into direct contact with the controllable fluid.

FIG. 3 illustrates another embodiment of controllable fluid rehabilitation device 20c. This embodiment is identical to the FIG. 1 embodiment, except that the flexible membrane or partition 50c has a shape capable of receiving a body part and which preferably substantially conforms to the shape of said body part, including partitions 50c having the shape of a glove, mitten, or sock. The opening 63c of the glove is stretched over a protrusion in the top 65c and secured in place by band 67c. Band 67c may be elastic, plastic, or metal. Top 65c is manufactured from a non-magnetic material, such as aluminum or plastic, such as aluminum or plastic, such as not to interrupt or affect the magnetic circuit 60c. The glove, etc., is pliable and flexible, preferably made of rubber, and formed of a large enough size such that the most users may easily fit their hand 40c or other body part into it. Attaching the glove, etc., as shown, eliminates the need for using a disposable glove or the like for each user. A sock or mitten-shaped membrane could also be used in a similar fashion.

Figure 4:
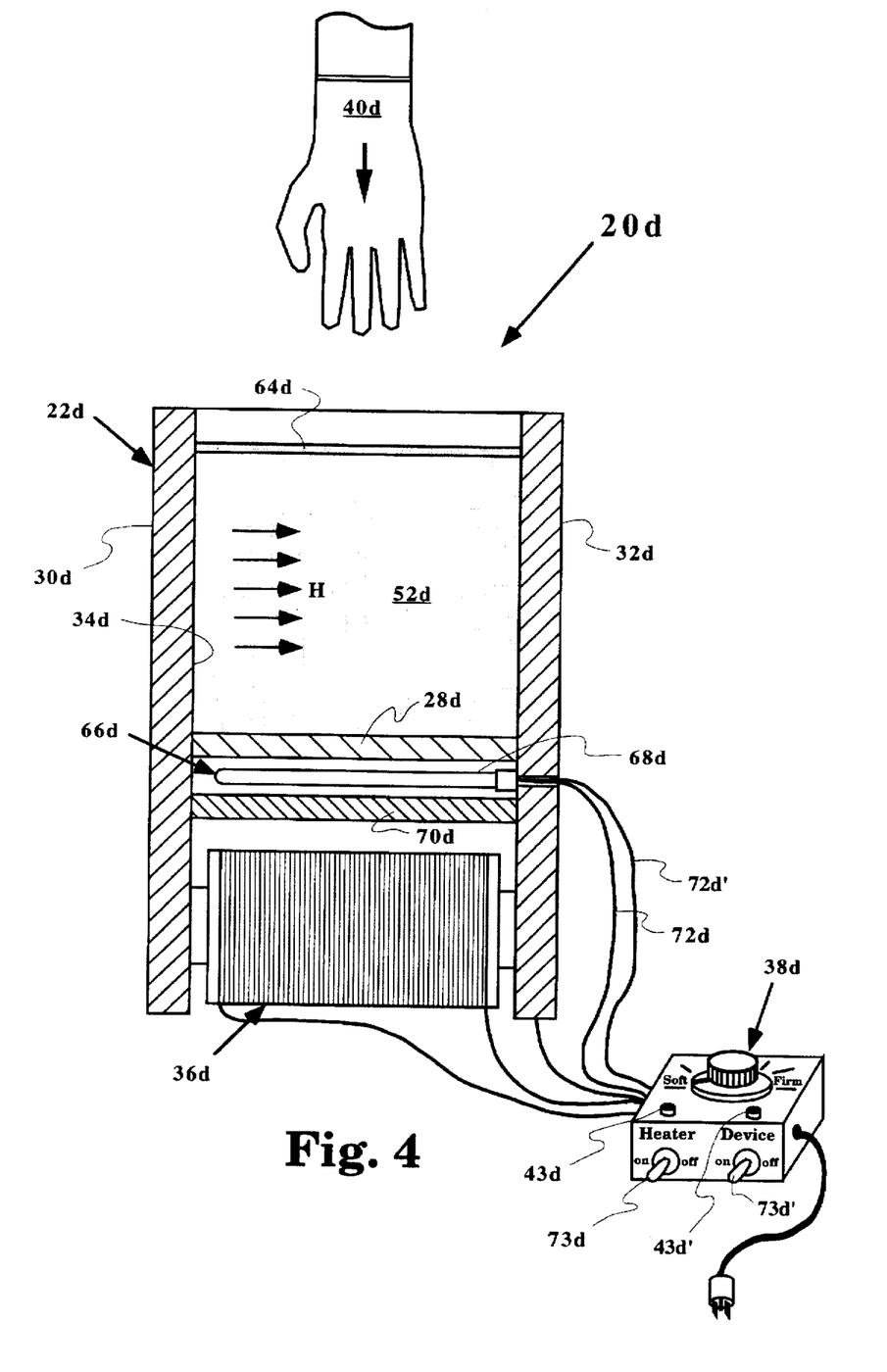
FIG. 4 is a cross-sectional side view of another embodiment of the rehabilitation device including a layer of lower density fluid which coats the user's skin to prevent direct contact with, and prevents evaporation of, the controllable fluid and which further includes a heating unit.

FIG. 4 illustrates another embodiment of controllable fluid rehabilitation device 20d. This embodiment is identical to the FIG. 1 except that a layer of a lower density fluid 64d, such as mineral oil, would prevent the fluid 52d from evaporating if, for example, the fluid 52d were a waterbased fluid. Other fluids 64d could be used that have low vapor pressure and lower density than the controllable fluid 52d.

In addition, this embodiment includes a heater unit 66d for heating the controllable fluid 52d to a comfortable or therapeutic temperature. The heater unit 66d is comprised of a heating element 68d which is preferably an AC resistive-type element, electrical cords 72d and 72d ' and an on-off switch 73d. A thermal insulator plate 70d is preferably used to keep the magnetic field generator 36d from being heated. Preferably, the bottom 28d would be manufactured from a material that inherently exhibits high thermal conductivity, such as copper or aluminum, thereby easily conducting the heat to the fluid 52d. Notably, the bottom 28d must also be non-magnetic. Generally, the fluid 52d would be heated to between about 95 degrees F and 135 degrees F. The resistive heater element 68d could be appropriately sized to achieve the desired temperature. Indicator lights 43d and 43d ' on controller 38d indicate when the heater unit 66d is on and when the unit is powered. Switches 73d and 73d ' control the heater unit 73d and resistance of the device 20d independently.

Figure 5:
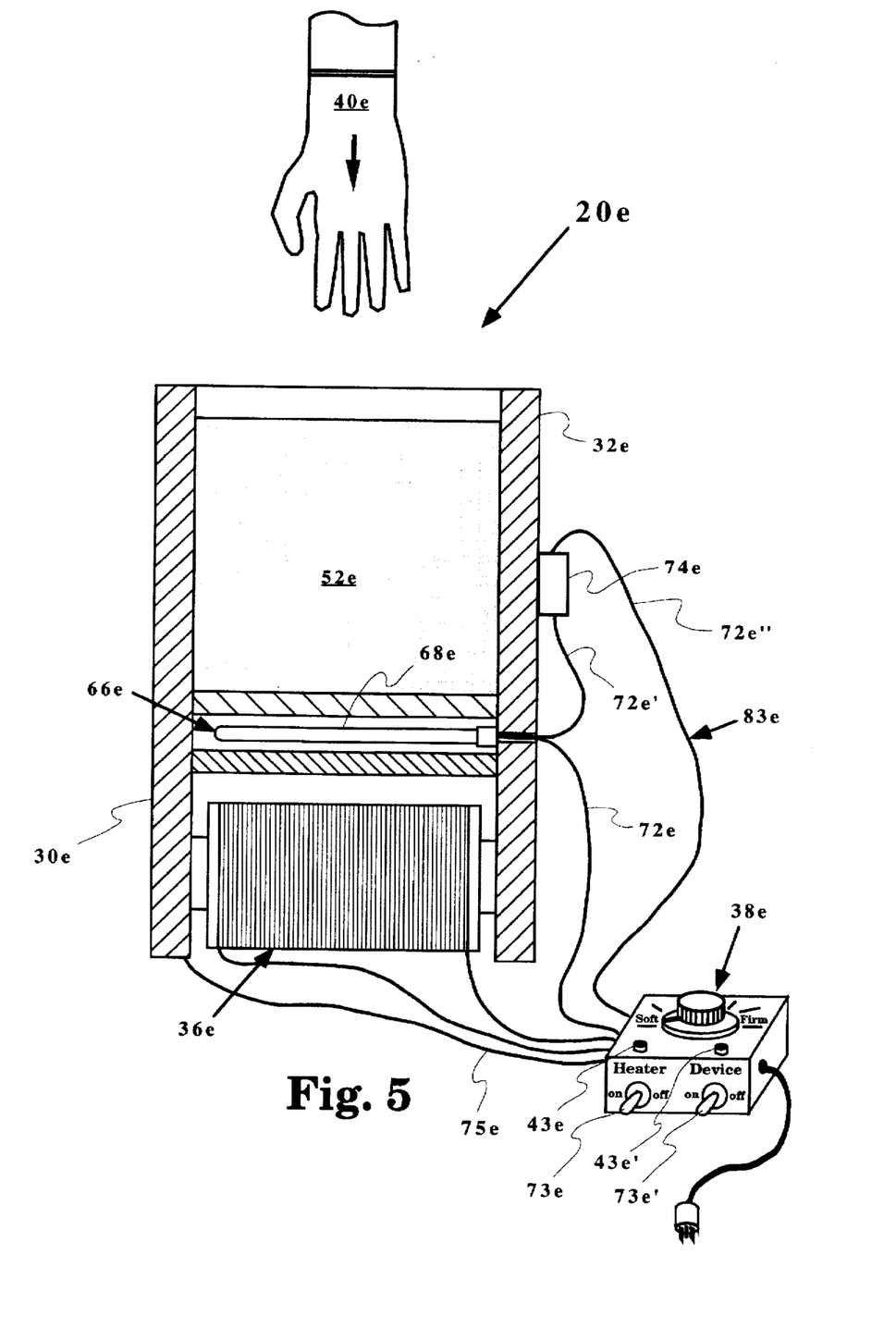
FIG. 5 is a cross-sectional side view of another embodiment of the rehabilitation device including a heating unit controlled by an on-off switching type thermostat.

FIG. 5 illustrates another embodiment of controllable fluid rehabilitation device 20e. This embodiment is identical to the FIG. 4 embodiment except that it includes a thermostat 74e for controlling the heating unit 66e. The AC current flows back and forth through cord 72e into heater element 68e heating the element, through cord 72e', into thermostat 74e and into cord 72e". Thermostat 74e is an on-off type switching thermostat. For example, when the temperature at the attachment point (thermostat 74e may be place anywhere it is convenient) reaches the set point (approximately 120 degrees F) of the thermostat 74e, the heater circuit 83e would be opened and the heating element 68e would no longer receive current. Therefore, the temperature can never exceed the set point temperature. A typical on-off thermostat would be a STANCOR P/N STO-120, available from White-Rodgers, St. Louis. A ground 75e would be added to first or second side 30e or 32e or bottom.

Figure 6:
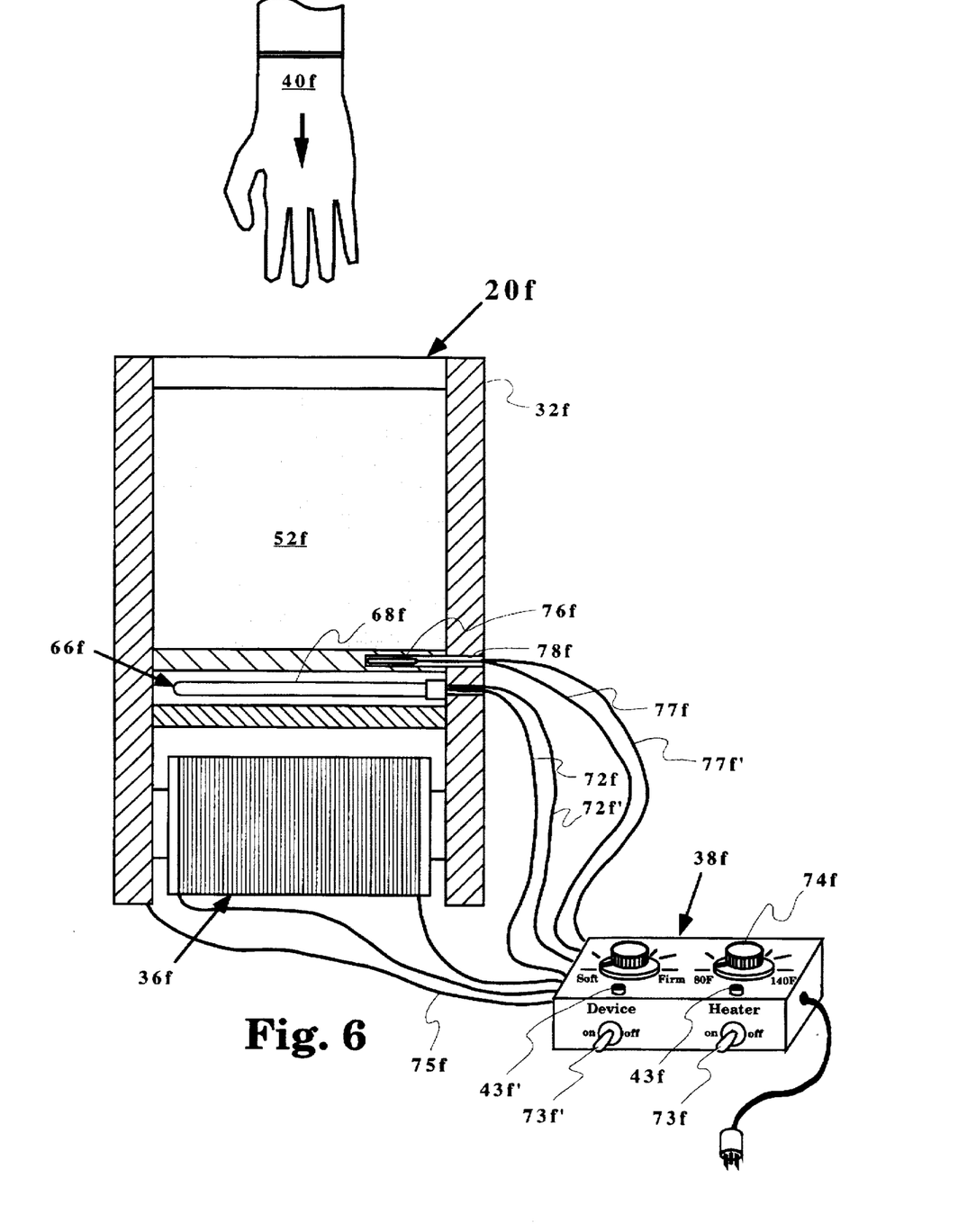
FIG. 6 is a cross-sectional side view of another embodiment of the rehabilitation device including a variable type thermostat for variably controlling the temperature of the controllable fluid.

FIG. 6 illustrates another embodiment of controllable fluid rehabilitation device 20f. This embodiment is identical to the FIG. 5 embodiment except that it includes an adjustable thermostat 74e for adjusting the temperature of the fluid 52f to a suitable therapeutic temperature. The heating unit 66f includes heating element 68f, a thermister 76f secured in a hole 78f placed as close to the fluid 52f as possible, and preferably in a material that has high thermal conductivity. Electrical signals indicative of the temperature at the location of the thermister 76f are received at the controller 38f via wires 77f, 77f'. The device 20f includes a on-off switches 73f and 73f' for both the device 20f and the heater unit 66e as well as indicators 43f and 43f' for the same.

Figure 7:
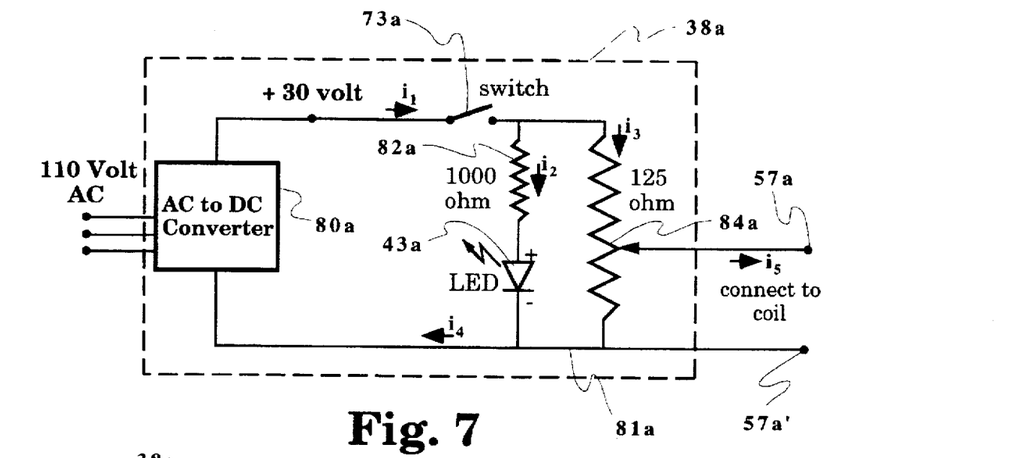
FIG. 7 is a electrical schematic of the controller for controlling the degree of resistance generated by the devices in FIG. 1 and FIG. 3–6.

FIG. 7 illustrates an electrical schematic of, for example, the portion of the controller used in conjunction with the devices shown in FIG. 1, 3, 4, 5, and 6 for controlling the level of magnetic field H intensity. The controller 38a is comprised of an AC to DC converter 80a to convert standard 110 Volt AC, such as from an electrical outlet, to 12–30 volt DC, and an indicator 43a such as an LED which is placed in series electrical relationship with a resistor 82a which preferably has a resistance of about 1000 ohm, thereby causing the indicator 43a to light when the switch 73a shown in the Off position (open) is throw to the On position (closed). The controller also includes, in parallel relationship with the branch including the resistor 82a and indicator 43a, a voltage divider 84a which has a maximum resistance value of approximately 125 ohm. Changing the position of the voltage divider 84a will change the voltage applied to the coil and, thus, the current is approximately according to the relationship: i=V/R. Wires 57a and 57a' of controller circuit 81a, for example, would attach to the coil 58a as shown in FIG. 1.

Figure 8:
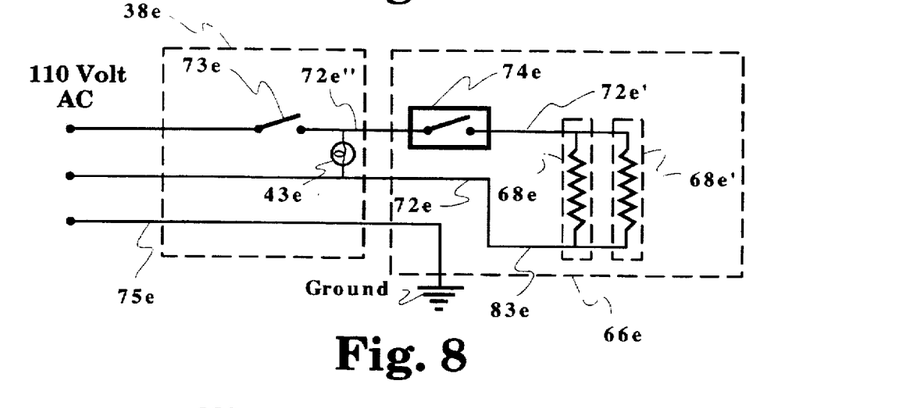
FIG. 8 is a electrical schematic of the heater circuit of the device shown in FIG. 5.

FIG. 8 illustrates an electrical schematic of the heater circuit 83e for heater unit 66e which is used in conjunction with the device 20e of FIG. 5. The heating unit 66e is comprised of a thermostat 74e and two heater elements 68e and 68e'. Heater elements 68e and 68e' are preferably resistive cartridge heaters such as McMaster-Carr model #3618K3 (225 Watt, 110 Volt). Thermostat 74e is preferably a Stancor STO-120 disc thermostat which opens above 120 degrees F. The on-off switch 73e and indicator 43e would be housed within the controller 38e. The heater unit 66e is powered by standard 110 Volt AC which is grounded via ground 75e. AC current is delivered between the elements by wires 72e, 72e' and 72e".

Figure 9:
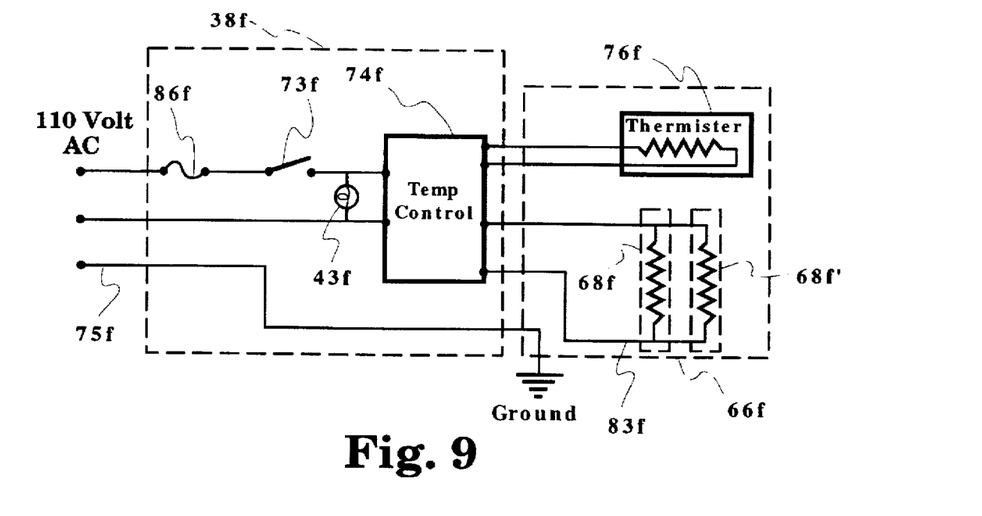
FIG. 9 is a electrical schematic of the adjustable heater unit of the device shown in FIG. 6.

FIG. 9 illustrates an electrical schematic of the heater unit 66f and controllable thermostat 74f used in the FIG. 6 embodiment. The temperature information is provided by a thermister 76f such as the 10K ohm thermister sensor manufactured by Nexus Custom Electronics, Inc., Model #27687-5. The thermostat 74f is preferably a proportional temperature controller manufactured by Nexus Custom Electronics, Inc., Model 72A. The heater circuit 83f may also include a fuse 86f, which preferably has a 15 amp fuse point. Heater elements 68f and 68f' are the same as described before. Fuse 86h, switch 73h, indicator 43f and thermostat 74f preferably would be housed within controller 38f.

In summary, the invention is a controllable fluid rehabilitation device for rehabilitation of complex human body parts comprising a housing having a reservoir formed therein for containing a sufficient volume of a magnetically controllable fluid for immersion of the body part. The controllable fluid experiences an apparent viscosity change when exposed to a magnetic field. The magnetic field is developed by a magnetic field generator which acts on the controllable fluid to change the viscosity thereof. A magnetic circuit directs the magnetic field such that it acts through the controllable fluid. The magnetic field generator may include a permanent magnet or an electromagnet. Further, a flexible partition or a low density fluid may be incorporated to prevent the user's body part from coming into direct contact with the controllable fluid and to prevent possible evaporation of the fluid, respectively. The device may be exposed to a low level magnetic field to prevent gravitational separation of the particles in the controllable fluid. In another aspect, a heater unit, which may include a thermostat, may used to heat the fluid.

While the preferred embodiment of the present invention has been described in detail, various modifications, alterations, changes and adaptations to the afore-mentioned may be made without departing from the spirit and scope of the present invention defined in the appended claims. It is intended that all such modifications, alterations and changes be considered part of the present invention.

What is claimed is:

1. A controllable fluid rehabilitation device for providing controllable resistive forces for rehabilitative exercise of a user's body part, comprising:
   (a) a housing having a reservoir formed therein;
   (b) a volume of a magnetically controllable fluid contained in said reservoir for immersion of the body part, said magnetically controllable fluid experiencing an apparent viscosity change when exposed to a magnetic field for providing said controllable resistive forces;
   (c) a magnetic field generator for generating said magnetic field which acts across said magnetically controllable fluid; and
   (d) a magnetic circuit of high magnetic permeability material for directing said magnetic field across said magnetically controllable fluid to bring about said apparent viscosity change.

2. A controllable fluid rehabilitation device of claim 1 wherein said magnetically controllable fluid is a magnetorheological fluid including a carrier fluid and magnetic particles.

3. A controllable fluid rehabilitation device of claim 1 wherein said magnetic field generator is a coil of wire wound about a high magnetic permeability core.

4. A controllable fluid rehabilitation device of claim 3 wherein said coil of wire is wound about a non-metallic bobbin to form a unit which is then slid over said high-magnetic-permeability core to form said magnetic field generator.

5. A controllable fluid rehabilitation device of claim 1 wherein said housing further includes a flexible partition attached thereto which separates the user's body part from direct contact with said magnetically controllable fluid as the user's body part is immersed.

6. A controllable fluid rehabilitation device of claim 5 wherein said flexible partition has a shape which substantially conforms to a shape of the body part.

7. A controllable fluid rehabilitation device of claim 1 wherein a layer of fluid which exhibits lower density than said magnetically controllable fluid floats on top of said magnetically controllable fluid.

8. A controllable fluid rehabilitation device of claim 1 wherein said housing contains a heating unit to heat said magnetically controllable fluid.

9. A controllable fluid rehabilitation device of claim 1 wherein said magnetic field generator is a permanent magnet.

10. A controllable fluid rehabilitation device of claim 1 wherein a magnetic field intensity applied to said controllable fluid is controlled by a shunt mechanism.

11. A controllable fluid rehabilitation device of claim 1 which includes means for exposing said magnetically controllable fluid to a low level magnetic field for preventing gravitational settling of particles contained in said magnetically controllable fluid within said chamber when said controllable fluid rehabilitation device is not in use.

12. A controllable fluid rehabilitation device of claim 1 wherein said housing includes a thermostat for controlling the temperature of said magnetically controllable fluid.

13. A controllable fluid rehabilitation device of claim 1 wherein a magnetic field intensity applied to said magnetically controllable fluid is controlled by an adjustable current source.

14. A controllable fluid rehabilitation device for providing controllable resistive forces for rehabilitative exercise of a user's body part, comprising:
   (a) a housing having a reservoir formed therein and a volume of a magnetorheological fluid contained in said reservoir for immersion of the body part, said magnetorheological fluid experiencing a change in apparent viscosity when exposed to a magnetic field for providing said controllable resistive forces;
   (b) a magnetic field generator having a coil wound about a high-magnetic-permeability core for generating said magnetic field which acts across said magnetorheological fluid; and
   (c) a magnetic circuit of high magnetic permeability material for directing said magnetic field through said magnetorheological fluid to bring about said change in apparent viscosity.

15. A controllable fluid rehabilitation device for providing controllable resistive forces for rehabilitative exercise of a user's body part, comprising:
   (a) a housing having a reservoir formed therein and a sufficient volume of a controllable fluid contained in said reservoir, for immersion of the body part, said controllable fluid experiencing a change in apparent viscosity when exposed to a magnetic field for providing said controllable resistive forces;
   (b) a magnetic field generator which is a permanent magnet for generating said magnetic field which acts on said controllable fluid; and
   (c) a magnetic circuit of high magnetic permeability material for directing said magnetic field through said controllable fluid to bring about said change in apparent viscosity.

* * * * *